(12) United States Patent
Yoshizako et al.

(10) Patent No.: US 6,805,793 B2
(45) Date of Patent: Oct. 19, 2004

(54) SEPARATORY MATERIAL WITH THE USE OF STIMULUS-RESPONSIVE POLYMER AND SEPARATION METHOD BY USING THE SEPARATORY MATERIAL

(75) Inventors: Kimihiro Yoshizako, Ibaraki (JP); Yoshikatsu Akiyama, Tokyo (JP); Katsuhiko Ueno, Ibaraki (JP); Teruo Okano, Chiba (JP)

(73) Assignees: Japan Chemical Innovation Institute, Tokyo (JP); The Agency of Industrial Science and Technology of the Ministry of International Trade and Industry, Tokyo (JP)

(*) Notice: Subject to any disclaimer, the term of this patent is extended or adjusted under 35 U.S.C. 154(b) by 0 days.

(21) Appl. No.: 10/434,899

(22) Filed: May 9, 2003

(65) Prior Publication Data

US 2003/0205527 A1 Nov. 6, 2003

Related U.S. Application Data

(62) Division of application No. 09/532,285, filed on Mar. 23, 2000, now Pat. No. 6,641,735.

(51) Int. Cl.[7] .............................................. B01D 15/08
(52) U.S. Cl. ............................... 210/198.2; 210/502.1; 210/635; 210/656
(58) Field of Search .................................. 210/635, 656, 210/657, 658, 659, 198.2, 502.1

(56) References Cited

FOREIGN PATENT DOCUMENTS

| EP | 0 534 016 | 3/1993 | ............. 210/198.2 |
|---|---|---|---|
| JP | 7-318551 | 12/1995 | ............. 210/198.2 |
| JP | 10-140722 | 5/1998 | ............. 210/198.2 |
| WO | WO87/06152 | 10/1987 | ............. 210/198.2 |
| WO | WO99/61904 | 12/1999 | ............. 210/198.2 |

OTHER PUBLICATIONS

Hosoya, K., et al. "Temperature–Controlled High–Performance Liquid Chromatography using a Uniformly Sized Temperature–Responsive Polymer–Based Pacling Material" Analytical Chemistry, vol. 67, No. 11, Jun. 1, 1995 pp. 1907–1911.

Yamamoto, et al, "Proc. 114th National Meeting of the Pharmaceutical Society of Japan" Tokyo, 1994, 160.

Kanazawa, H., et al. "Temperature–Responsive Chromatography" Yakugaku Zasshi, 117 (10–11) 1997 pp. 817–824.

Kanazawa, H., et al. "Temperature–Responsive Chromatography Using Poly(N–isopropylacrylamide)–Modified Silica" Analytical Chemistry, 68(1) (1996) pp. 100–105.

Kanazawa, H., et al. "Temperature–Responsive Liquid Chromatography. 2. Effects of Hydrophobic Groups in N–isopropylacrylamide Copolymer–Modified Solica" Analytical Chemistry, 69(5) (1997) pp. 823–830.

Kanazawa, H., et al. "Analysis of peptides and proteins by temperature–responsive chromatographic system using N–isopropylacrylamide polymer–modified columns" Journal of Pharmaceutical and Biomedical Analysis, 15(1997) pp. 1545–1550.

Yakushiji, T., et al. "Graft Architectural Effects on Thermoresponsive Wettability Changes of Poly(N–isopropylacrylamide)–Modified Surfaces" Langmuir, 14(16) (1998) pp. 4657–4662.

(List continued on next page.)

*Primary Examiner*—Ernest G. Therkorn
(74) *Attorney, Agent, or Firm*—Royal N. Ronning, Jr.; Stephen G. Ryan; Yonggang Ji

(57) ABSTRACT

A novel method for separating a target substance, for example, metal ion, drug or biological component is provided. According to the method, the surface of a packing undergoes a chemical or physical environmental change under a physical stimulus so that the interaction of a substance interacting with the target substance is reversibly changed in an aqueous solution, thus effecting separation.

4 Claims, 2 Drawing Sheets

OTHER PUBLICATIONS

Kanazawa, H., et al. "Temperature–responsive chromatography" Trends in Analytical Chemistry, vol. 17, No. 7, 1998 pp. 435–440.

Yakushiji, T., et al. "Effects of Cross–Linked Structure on Temperature–responsive Hydrophobic Interaction of Poly(N–isopropylacrylamide) Hydrogel–Modified Surfaces with Steriods" Analytical Chemistry, 71(6) (1999) pp. 1125–1130.

Galaev, I., et al. "Temperature–induced displacement of proteins from dye–affinity columns using an immobilized polymeric displacer" Journal of Chromatography A. Elsevier Science B.V. 684 (1994) pp. 37–43.

Gewehr, M., et al. "Gel permeation chromatography using porous glass beads modified with temperature–responsive polymers" Macromolecular Chemistry and Physics 193 (1992) pp. 249–256.

SEPARATORY MATERIAL WITH THE USE OF STIMULUS-RESPONSIVE POLYMER AND SEPARATION METHOD BY USING THE SEPARATORY MATERIAL

The application is a divisional application of U.S. patent application Ser. No. 09/532,285 filed Mar. 23, 2000, now U.S. Pat. No. 6,641,735 the entire disclosure of which is hereby incorporated by reference.

TECHNICAL FIELD

This invention relates to a novel separation method for separating a target substance (metal ions, drugs, biological components, etc.) with the use of a separatory material wherein the interaction force of a substance (ligand) interacting with the target substance can be reversibly changed in an aqueous system due to a structural change or a polarity change of a stimulus-responsive polymer under a physical stimulus, and a separatory material such as a packing to be used in this method.

BACKGROUND OF INVENTION

The most effective and efficient means employed at present for separating and purifying biological components and drugs include ion exchange chromatography, reversed phase chromatography, affinity chromatography, etc. In recent years, bioengineering procedures have made remarkable advances and physiologically active substances (recombinant proteins, glycoproteins, etc.) are produced thereby on a mass scale. Under these circumstances, there is a growing requirement for methods by which these products can be quickly and efficiently separated and purified without inactivation.

In the chromatographic techniques as cited above, however, target substances (biological components, drugs, recombinant proteins, glycoproteins, etc.) are eluted by changing the salt concentration, organic solvent concentration, pH value, etc. of eluents. It is known that, in such a case, the pH value, organic solvent, etc. frequently bring about severe conditions for the target substance and thus lower the recovery yield thereof. In addition, the salt, organic solvent, pH- regulating agent, etc. employed in eluting the target substance should be finally eliminated by desalting, drying, etc. Therefore, an additional step is required, after the completion of the separation and purification of the target substance, to perform an operation for eliminating the salt, organic solvent, pH-regulating agent, etc. As a result, the activity and yield of the final product are often lowered.

When the target substance is eluted by a chemical means with the use of a salt, an organic solvent, a pH-regulating agent, etc., the chemical (i.e., the salt, organic solvent, pH-regulating agent, etc.) contained in the eluent causes the above-mentioned problems of inactivation, a decrease in the yield, etc. It is expected that if a physical change induced by, for example, heat, light or a magnet could affect the elution of a target substance, the target substance would be eluted not by a chemical means but by a physical one, thus solving the problems of inactivation, a decrease in the yield, etc.

Recently, separation material comprising stimulus-responsive polymers covalently attached to ion exchanging groups have been described. See for instance JP application 140722/98 and corresponding WO applicationWO99/61904

Galaev et al (J. Chromatog. A 684 (1994) 37–43 describe temperature elution of lactate dehydrogenase (LDH) in a chromatographic system in which a dye (ligand) is covalently attached to a base matrix which also carries a physically adsorbed temperature responsive polymer.

Hofman et al., (WO 8706152) describes a separation method in which the ligand is attached to a temperature responsive polymer. Binding and elution of the target substance occur at the same side of the critical solution temperature.

There are also a number of publications describing chromatography based on separatory material comprising stimulus-responsive polymers but without having a ligand covalently attached to the temperature-responsive polymer. Gewehr et al (Macromolecular Chemistry and Physics 193 (1992) 249–256) describes gel chromatography on porous silica beads coated with a temperature-responsive polymer. Hosoya et al (Anal. Chem. 67 (1995) 1907–1911); Yamamoto et al. (Proc. 114$^{th}$ National Meeting of the Pharmaceutical Society of Japan, Tokyo (1994) 160; Kanazawa et al (Yakugaku Zasshi 117 (10–11) (1997) 817–824; Kanazawa et al (Anal. Chem. 68(1) (1996) 100–105); Kanazawa et al (Anal. Chem. 69(5) (1997) 823–830); Kanazawa et al (J. Pharm. Biomed. Anal. 15 (1997) 1545–1550); Yakushiji et al (Langmuir 14(16) 1998) 4657–466268); Kanazawa et al (Trends Anal. Biochem. 17(7) (1998) 435–440); Yakushiji et al (Anal. Chem. 71(6) 1999) 1125–1130); Grace & Co (EP 534016); Okano (JP 6-108643) describe reversed phase chromatography on matrices covered by a thermoresponsive olymer for the separation of biomolecules. The matrices may be porous. The hydrophobic groups utilized are inherent in the polymer as such. There is no ligand that has been covalently attached to the polymer after polymerisation.

SUMMARY OF INVENTION

From this point of view, the present inventors have conducted intensive studies and developments on the elution of a target substance by a physical means to thereby solve the above problems. As a result, they synthesized a composite material comprising a stimulus-responsive polymer with a ligand molecule by binding poly(N-isopropylacrylamide) to a molecule (i.e., a ligand molecule) capable of interacting with a target substance. Subsequently they have found out that use of this composite material makes it possible to obtain a separatory material which undergoes a change in the interaction between the ligand molecule and the target substance under a physical stimulus. The present invention has been completed based on this finding.

The present invention relates to a method for separating substances characterized in that a composite material comprising a stimulus-responsive polymer and a substance (ligand) interacting with a target substance undergoes a physical or chemical change of the stimulus-responsive polymer under a physical stimulus so that the environment of the interaction between the target substance and the molecule interacting therewith is physically or chemically changed. This means that the target substance can be released from the ligand and also from the separatory material, thus effecting separation of the target substance from the composite material or separatory material.

The present invention further relates to a method for separating substances characterized by comprising (a) binding a target substance on a stationary phase of a separatory material (including chromatographic packing) chemically modified with a composite material comprising a stimulus-responsive polymer and a substance (ligand) interacting specifically with the target substance; then (b) changing continuously or stepwise the temperature, preferably by external means, to thereby weaken the interaction between the ligand and the target substance; and eluting the chromatographic packing by a mobile phase while maintaining a temperature which permit a weakened interaction between the ligand and the target substance thus effecting separation. The mobile phase may be a liquid, for instance aqueous.

The present invention further relates to a separatory material (for example, a chromatographic packing) wherein the ability of a substance to recognize a molecule can be changed due to a physical stimulus.

Another embodiment of the invention is a method for the separation of one or more target substances from a liquid. This embodiment comprises the steps of substances from (a) bringing a liquid sample (I) containing a target substance in contact with a separation medium/separatory material (including a chromatographic packing) which is functionalized with a ligand which is capable of binding to the target substance, said contact being under conditions permitting binding of said target substance to said ligand;

(b) contacting said carrier with a liquid (II) not containing said at least one target substance under conditions such that the target substance is released from said ligand to liquid (II).

Between steps (a) and (b) the liquid sample is preferably separated from the separatory material which in turn may be washed before step (b). After step (b), liquid (II) may be separated from the separatory material. The target substance, if so desired, may be worked up from liquid II.

With respect to target substances in form of biological molecules such as those having nucleotide structure (including nucleic acids), polypeptide structure (including proteins), carbohydrate structure, steroid structure etc the liquids used typically have been aqueous. This embodiment of the invention is characterized in that (i) said separatory material comprises a stimulus-responsive polymer as defined elsewhere in this specification, which polymer has been functionalized with the ligand, preferably by covalent attachment of the ligand after the polymer has been formed, and (ii) subjecting in step (a) and at least during binding of the target substance to the ligand, the separatory material to a stimulus at a level/intensity at which the stimulus-responsive polymer in a conformation enhancing binding of the target substance to the ligand, and (iii) subjecting in step (b) and at least during release of the target substance from the ligand the separatory material to a stimulus at a level/intensity at which the stimulus-responsive polymer is in a conformation hindering binding of the target substance to the ligand.

The level/intensity of the stimulus is on opposite sides of the critical level/intensity for the stimulus-sensitive polymer used and other conditions applied in the respective step. The process can be made cyclic in case step a is repeated after step b, typically after extra washing/regeneration steps and equilibration steps.

Various embodiments of the inventive method may be carried out in a batch-wise or a chromatographic mode. Chromatographic modes, for instance, may be carried out by permitting the various liquids in plug flow (mobile phase) to pass through a bed of the separatory material while subjecting the bed to the appropriate stimulus for the individual steps and stimulus-responsive polymer used. The bed may be a porous monolith or a bed of packed or fluidised particles. Batch-wise modes in particular concerns suspended particles in combination with turbulent flow and/or liquids.

DETAILED DESCRIPTION OF INVENTION

Figure 1:
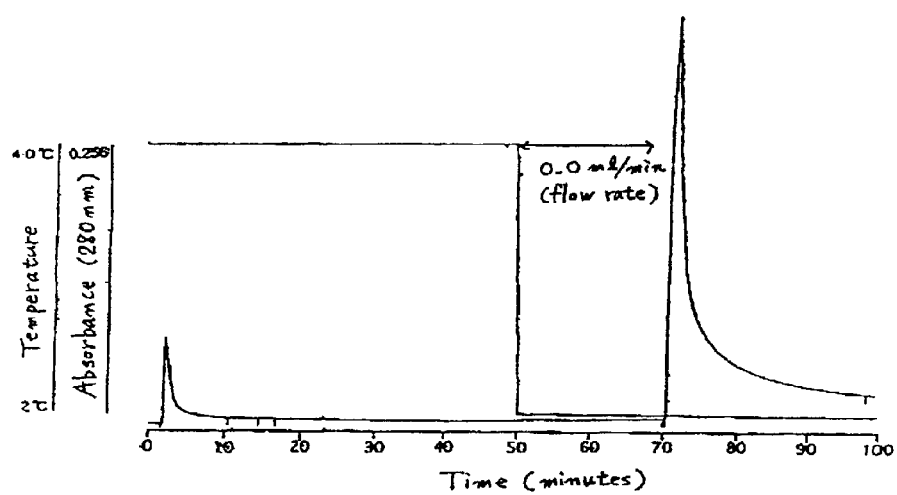
FIG. 1 provides a chromatogram showing the elution of BSA molecules held on CB molecules from a p(NIPAAm)-AmCB column with temperature change.

The physical stimulus to be used in the method according to the present invention is exemplified by temperature. Namely, the molecular-recognizability of a substance interacting with a target substance can be changed under a temperature change by using, for example, a composite material comprising a heat-responsive polymer. As an example thereof, a chromatographic packing chemically modified with a composite material of a polyalkylamide having a terminal functional group, for example, amino, carboxyl or hydroxyl group may be cited. A chemically modified carrier is exemplified by a silica carrier.

Depending on the particular stimulus-responsive polymer used other stimulus may apply, for instance light, magnetic field, electrical field, pH, etc. Stimulus-responsive polymers are often called "intelligent polymers".

Stimulus-responsive polymers are characterized in that they upon being subjected to the correct stimulus of the correct intensity or level (critical level of stimulus or critical intensity of stimulus) undergo a conformational and reversible change of their physico-chemical properties. The change may be a switch from a pronounced hydrophobicity to a pronounced hydrophilicity or vice versa. The exact level/intensity and kind of the required stimulus depend on the structure of the polymer and will often also depend on other conditions (solvent, solutes such as salts etc). The most well-known and most utilized polymers of this kind respond to heat (thermo-responsive or temperature-responsive polymers). Temperature-responsive polymers are recognized by having a sharp temperature limit at which they switch from a pronounced hydrophilic state to a pronounced hydrophobic state and vice versa. For temperature-responsive polymer in solution the change in conformation/physico-chemical properties occurs at the so called critical solution temperature (CST).

For a temperature responsive polymer in aqueous media there is a lower critical solution temperature (LCST) or an upper critical solution temperature (UCST). For a polymer having a LCST, the polymer change from a hydrophilic conformation to a hydrophobic conformation when the temperature is passing the LCST from below. For a polymer having an UCST, the change is the opposite when the temperature is passing the UCST from below. The exact value of the LCST and UCST depend on the polymer and also on other conditions applied (solvent, other solutes etc).

As discussed above one of the characteristic features of the invention when a temperature-sensitive polymer is used is that the binding to and the release from the ligand is performed at opposite sides of an applicable CST.

The stimulus-responsive polymer preferably has an insignificant affinity for the target substance compared to the affinity between the target substance and the covalently attached ligand. Preferably there is no significant affinity between the ligand and the thermoresponsive polymer.

Examples of the fundamental constituent unit of the temperature-responsive polymer include homopolymers and copolymers of N-alkyl(meth)acrylamide such as N-isopropyl(meth)acrylamide, N-(meth)acryloylpiperidine, N-propyl(meth)acrylamide, N,N-diethyl(meth)acrylamide, N-cyclopropyl(meth)acrylamide, N-(meth)acryloylpyrrolidine, N,N-ethylmethyl(meth)acrylamide and N-ethyl(meth)acrylamide, and copolymers thereof with monomers containing functional groups such as carboxyl, amino, hydroxysuccimido, thiol, imino and epoxy groups for ensuring chemical composition with molecules interacting with target substances.

Examples of the polyalkylacrylamide to be used in the method according to the present invention include poly(N-isopropylacrylamide)-dye composite materials.

Examples of the target substance and the molecule interacting with the target substance include biological components composed of amino acids, saccharides, nucleic acids, etc. and organic compounds having a molecular weight of not more than 1,000. Although the amount of the ligand molecule to be chemically composed with the stimulus-responsive polymer may be arbitrarily controlled, it preferably amounts to 0.1 to 50% based on the whole composite. The physical or chemical properties of the stimulus-responsive polymer can be varied by controlling the amount of the molecule interacting with the target substance to be composed therewith. For example, a poly(N-isopropylacrylamide) homopolymer has a low limit critical temperature of about 32° C. which can be varied by controlling the amount of the molecule interacting with the target substance to be composed therewith.

Separatory Materials (e.g. Chromatographic Packings)

The separatory material to be used in the inventive method comprises a base matrix (carrier) which may be based on organic and/or inorganic material. In case the liquid used is aqueous, the base matrix is preferably hydrophilic. This in particular applies to target substances that are biomolecules of the kind discussed above.

The base matrix is preferably based on a polymer, which preferably is insoluble and more or less swellable in water. Hydrophobic polymers that have been derivatized to become hydrophilic are included in this definition. Suitable polymers are polyhydroxy polymers, e.g. based on polysaccharides, such as agarose, dextran, cellulose, starch, pullulan, etc. and completely synthetic polymers, such as polyacrylic acid amide, polymethacrylic acid amide, poly(hydroxyalkylvinyl ethers), poly(hydroxyalkylacrylates) and polymethacrylates (e.g. polyglycidylmethacrylate), polyvinylalcohols and polymers based on styrenes and divinylbenzenes, and copolymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerization of monomers exhibiting groups which can be converted to OH, or by hydrophilization of the final polymer, e.g. by adsorption of suitable compounds, such as hydrophilic polymers.

Suitable inorganic materials to be used in base matrices are silica, zirconium oxide, graphite, tantalum oxide etc.

Preferred matrices lack groups that are unstable against hyrolysis, such as silan, ester, amide groups and groups present in silica as such.

The matrix may be porous or non-porous. This means that the matrix may be fully or partially permeable (porous) or completely impermeable to the compound to be removed (non-porous).

The pores may have sizes $\geq 0.1$ $\mu$m, such as $\geq 0.5$ $\mu$m, by which is meant that a sphere $\geq 0.1$ $\mu$m respective $\geq 0.5$ $\mu$m in diameter is able to pass through. An applied liquid may be able to flow through this kind of pore system (convective pore system). In case the support matrix is in form of beads packed to a bed, the ratio between the pore sizes of the convective pore system and the diameter of the particles typically is in the interval 0.01–0.3, with preference for 0.05–0.2. Pores having sizes $\geq 0.1$ $\mu$m, such as $\geq 0.5$ $\mu$m, are often called macropores.

The base matrix may also have pores with sizes $\leq 0.5$ $\mu$m, such as $\leq 0.1$ $\mu$m by which is meant that only spheres with diameters $\leq 0.5$ $\mu$m, such as $\leq 0.1$ $\mu$m, can pass through. Pores having sizes $\leq 0.5$ $\mu$m, such as $\leq 0.1$ $\mu$m, are often called micropores.

In a particularly interesting embodiment of the present invention, the base matrix is in the form of irregular or spherical particles with sizes in the range of 1–1000 $\mu$m, preferably 5–50 $\mu$m for high performance applications and 50–300 $\mu$m for preparative purposes.

The base matrix may also be in form of a monolith having at least macropores as defined above. Alternative geometric forms are the interior walls of tubes and the like The stimulus responsive polymer as defined above may be attached to the base matrix on its outer surfaces and/or on its interior surfaces (macropore and/or micropore surfaces). It may also be part of the polymer constituting the base matrix as such. The stimulus responsive polymer may be attached to the base matrix by physical adsorption and/or covalent attachment, preferably the latter.

Ligands

Ligands may be attached to the stimulus responsive polymer either before or after the polymer has been attached to or incorporated into the base matrix. Attachment to the stimulus polymer may be by affinity bonds or by covalent bonds, preferably the latter. One typical kind of ligands binds to the target substance by more or less pure ionic (electrostatic) interactions. Alternatively the binding includes more complex interactions such as affinity binding (affinity adsorption). For ionic interactions the ligands comprises positively or negatively charged entities (ion exchange; the immobilised entity being selected among primary, secondary, tertiary and quaternary ammonium, sulphonate, sulphate, phosphonate, phosphate, carboxy etc groups). More complex interactions are illustrated by the ligand being on of the affinity members in the pairs, (a) antibodies and antigens/haptens, (b) lectins and carbohydrate structures, (c) IgG binding proteins and IgG, (d) polymeric chelators and chelates, (e) complementary nucleic acids, Affinity members also include entities participating in catalytic reactions, for instance enzymes, enzyme substrates, cofactors, cosubstrates etc. Members of cell-cell and cell-surface interactions and a synthetic mimetics of bioproduced affinity members are also included. The term ligand also includes more or less complex organic molecules, for instance dyes, that binds through affinity to complex biomolecules, for instance having oligo or polypeptide structure (including proteins), oligo and polynucleotide structure (including nucleic acids), oligo- or polysaccharide structures etc.

EXAMPLES

The present invention will now be explained in more detail with reference to examples which are not intended to limit the present invention.

Example 1

Bovine serum albumin (BSA) used as the target substance and Cibacron Blue (CB) as the molecule interacting with the target substance were composed with a heat-responsive polymer and the change in interaction with the target substance by a temperature stimulus was evaluated by a chromatographic technique. As a result, it was confirmed that the interaction changed by a temperature change to dissociate the CB molecular from BSA.

1. Synthesis of Polymer (1-1-a) Synthesis of Poly(N-isopropyl acrylamide/N-acryloxy-succinimide) [Hereinafter Referred to As Poly(IPAAm-co-ASI)] Having Terminal Carboxyl Group In a polymerization tube were charged 15 g of N-isopropyl acrylamide, 1.24 g of N-acryloxy succinimide as the monomer having a functional group, 0.28 g of mercaptopropionic acid (MPA) as the chain transfer agent, 82 mg of 2,2-azobisisobutyronitrile (AIBN) as the polymerization initiator and 500 ml of tetrahydrofuran (THF), and the polymerization tube with the cock closed was placed in liquid nitrogen and completely frozen. Then, the cock was opened and the polymerization tube was deaerated by a vacuum pump. Subsequently, the cock was closed again and the polymerization tube containing the reaction solution was placed in propanol to completely dissolve the sample in the polymerization tube. This operation was repeated three times (freeze-thaw deaeration). Thus, the polymerization tube in which the sample was thoroughly deaerated and was under reduced pressure was placed in a shaking thermostatic chamber at 70° C. to effect radical polymerization for two hours and as a result, a copolymer having a carboxyl group at one terminal was obtained. After the reaction, the copolymer was reprecipitated by adding the reaction solution dropwise to ice-cooled diethyl ether to obtain a polymer. The resulting polymer was separated by filtration, dried under reduced pressure overnight at normal temperatures, then, dissolved in a THF solution and purified again in diethyl ether. The polymer thus obtained was separated by filtration, passed through a gel filtration column to dispense the desired polymer. The resulting polymer was freeze-dried, then dissolved in a THF solvent, reprecipitated and separated by filtration. The polymer thus obtained was dried overnight under reduced pressure at normal temperature to obtain the desired polymer.

(1-1-b) Composing of Aminohexyl Cibacron Blue (Hereinafter Referred to As "AmCB") with Poly(IPAAm-co-ASI) Having Terminal Carboxyl Group In 100 ml of pyridine were dissolved 5.0 g of the synthesized polymer and 0.43 g of aminohexyl Cibacron Blue and stirred at room temperature for 24 hours, and 2 ml of isopropylamine was added thereto and the resulting solution was further stirred for 24 hours to compose aminohexyl Cibacron Blue with the polymer. After completion of stirring, the solvent was removed by a rotary evaporator and the composite material was freeze-dried. After the drying, the composite material was dissolved in purified water to dispense the desired composite material by gel filtration which was then free-dried to obtain the desired polymer.

(1-1-c) Active Esterification (Succinylation) of Terminal Carboxyl Group of Poly(IPAAm-co-ASI) Having Terminal Carboxyl Group/Aminohexyl Cibacron Blue(AmCB) Composite Material [Hereinafter Referred to As "p(NTPAAm)-AmCB"]

In a 300 ml eggplant-shape flask were placed 3 g of the synthesized copolymer, 0.5 g of N,N-dicyclohexylcarbodiimide and 0.5 g of N-hydroxysuccinimide and dissolved in 100 ml of THH and stirred at room temperature for 48 hours. The dicyclohexylurea to be separated out by a by-product during stirring was removed by filtration and the reaction product was finally reprecipitated in diethyl ether to obtain a p(NIPAAm)-AmCB composite material in which one terminal was succinylated.

(1-1-d) Introduction of Succinylated p(NIPAAm)-AmCB Composite Material to Carrier (1)

In 100 ml of 1,4-dioxane was dissolved 1.0 g of the succinylated p(NIPAAm)-AmCB composite material and fixed on aminopropyl silica gel at room temperature. After stirring the mixture for 24 hours, 1.0 g of fresh succinylated p(NIPAAm)-AmCB composite material was dissolved in 100 ml of 1,4-dioxane and then reacted with the resulting gel for 24 hours. This operation was repeated once again and finally, the reacted gel was separated by filtration and thoroughly washed with an organic solvent such as dimethylformamide and methanol and a 66.7 mM phosphoric acid buffer solution containing 100 mM to 500 mM NaCl to obtain the desired packing.

(1-1-e) Introduction of p(NIPAAm)-AmCB Composite Material to Carrier (2)

To 0.65 g of the copolymer whose one terminal was carboxylated were added 30 mg of N-ethoxycarbonyl-2-ethoxy-1,2-dihydroquinone (EEDQ), 0.8 g of aminopropyl silica and 100 ml of THF, subjected to nitrogen replacement for 20 minutes and then, stirred overnight at room temperature. After completion of the stirring, silica particles were separated by filtration. In the same manner, 0.6 g of the copolymer whose one terminal was carboxylated, 30 mg of N-ethoxycarbonyl-2-ethoxy-1,2-dihydroquinone (EEDQ) and 100 ml of THF were added to the resulting silica particles and the mixture was subjected to nitrogen replacement for 30 minutes and then, stirred overnight at room temperature. After completion of the stirring, silica particles were separated by filtration and thoroughly washed with an organic solvent such as dimethylformamide and methanol and a 66.7 mM phosphoric acid buffer solution to obtain a p(NIPAAm)-AmCB composite material-fixed silica column packing.

2. Column Packing

In a packing solvent prepared at a volume ratio of methanol:2-propanol:water of 1:1:1 was dispersed 0.6 g of the p(NIPAAm)-AmCB composite material-fixed silica and charged in a column packing packer. Packing into a stainless column of 4.6×30 mm was carried out at a pressure of 100 kg/cm$^2$ for the initial 25 ml and at a pressure of 400 kg/cm$^2$ for the rest.

3. Preparation of Sample (3-1) Preparation of Bovine Serum Alubumin (BSA) Sample BSA was dissolved in a 66.7 mM phosphoric acid buffer solution having a pH of 7.0 to adjust the concentration at 7.60 mg/ml.

4. HPLC Measuring Conditions

Figure 2:
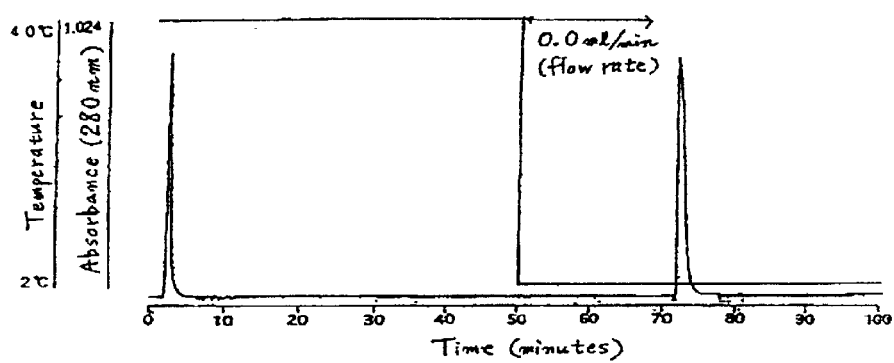
FIG. 2 provides a control chromatogram with the use of a p(NIPAAm) column.

Column: p(NIPAAm)-AmCB
   Mobile Phase: 66.7 mM phosphoric acid buffer solution having a pH of 7.0
   Flow Rate: 0.2 ml/min
   Temperature Condition: 40° C. to 2° C.
   Measuring Wavelength: 280 nm 5. Results A typical chromatogram in the case of injecting 20 µl of a 7.6 mg/ml BSA solution into the p(NIPAAm)-AmCB column is shown in FIG. 1. After 50 minutes from the injection, the temperature was lowered from 40° C. to 2° C. Further, to equilibrate the temperature at 20° C., feeding of the solution was stopped for 20 minutes and then, the flow rate was returned to the initial flow rate of 0.2 ml/min. At 71.25 minutes the elution peak was observed and the eluate was brown by micro BCA protein assay and the molecular weight was equal to that of BSA from the results of the analysis of the gel filtration chromatography and thus, it was confirmed that the elution peak was that of BSC. Further, an experiment of using a silica column to which p(NIPAAm) alone had been fixed was carried out in the same manner as in using the p(NIPAAm)-AmCB column but BSA did not adhere as and passed through the column shown in FIG. 2. It was also confirmed by micro BCA protein assay that the peak at 70.9 minutes was not for BSA. Since this peak was also recognized in the case of a control sample free of BSA, it was thought that this peak was for impurities. From these results it was confirmed that the interaction between a target substance and a molecule interacting with the target substance by a temperature-stimulus could be controlled by a physical stimulus such as a temperature change.

INDUSTRIAL APPLICABILITY

The separation method with the use of the separatory material according to the present invention has the following advantages.

1) Different from the chemical elution methods employed in the conventional chromatographic techniques, no severe chemical condition is needed therein and thus a useful biopolymer can be recovered at a high yield.

2) By changing an interaction due to a physical stimulus, an interaction differing from the inherent one with a target substance can be induced.

3) In the case of the separatory material of the present invention, no post-elution treatment (desalting, pH regulation, etc.) is needed, as in the case of the conventional affinity chromatography.

4) A packing can be quickly regenerated, compared with the conventional affinity chromatographic carriers.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A material for use in separation methods comprising a stimulus-responsive polymer and a substance interacting specifically with a target substance, wherein said stimulus-responsive polymer undergoes a structural change upon a physical stimulus such that the interaction of the substance interacting specifically with the target substance is affected, thereby causing a reversible change in the interaction force with the target substance due to the physical stimulus.

2. The material as claimed in claim 1, wherein said physical stimulus is a temperature change.

3. The material as claimed in claim 1, wherein the stimuluse responsive polymer is a polyalkylamide polymer or copolymer having a terminal functional group.

4. The material in claim 3, wherein the terminal functional group is an amino group or a carboxyl group.

* * * * *